(12) United States Patent
Glukhovsky

(10) Patent No.: US 7,813,789 B2
(45) Date of Patent: *Oct. 12, 2010

(54) IN-VIVO IMAGING DEVICE, OPTICAL SYSTEM AND METHOD

(75) Inventor: Arkady Glukhovsky, Santa Clarita, CA (US)

(73) Assignee: Given Imaging Ltd., Yoqneam (IL)

( * ) Notice: Subject to any disclaimer, the term of this patent is extended or adjusted under 35 U.S.C. 154(b) by 872 days.

This patent is subject to a terminal disclaimer.

(21) Appl. No.: 11/221,841

(22) Filed: Sep. 9, 2005

(65) Prior Publication Data
US 2007/0002135 A1    Jan. 4, 2007

Related U.S. Application Data

(63) Continuation-in-part of application No. 10/879,483, filed on Jun. 30, 2004, which is a continuation-in-part of application No. 10/009,837, filed as application No. PCT/IL00/00349 on Jun. 15, 2000, now Pat. No. 6,836,377, and a continuation-in-part of application No. 10/478,252, filed as application No. PCT/IL02/00391 on May 20, 2002.

(30) Foreign Application Priority Data

Jun. 15, 1999  (IL) ..................... 130486
May 20, 2001  (IL) ..................... 143258

(51) Int. Cl.
*A61B 6/00* (2006.01)
(52) U.S. Cl. ............................ 600/476
(58) Field of Classification Search .......... 600/476, 600/160, 176; 356/708, 727
See application file for complete search history.

(56) References Cited

U.S. PATENT DOCUMENTS 3,289,779 A    12/1966   Feucht
(Continued)

FOREIGN PATENT DOCUMENTS

DE             323 006      7/1920
(Continued)

OTHER PUBLICATIONS

Office Action of Application No. 05026710.3-1265 dated Jun. 2, 2008.
(Continued)

*Primary Examiner*—Long V Le
*Assistant Examiner*—Jacqueline Cheng
(74) *Attorney, Agent, or Firm*—Pearl Cohen Zedek Latzer, LLP

(57) ABSTRACT

An in-vivo device may include an optical system, and a method for viewing in-vivo sites. A dome or cover may cover an end of the device, protecting optical elements such as illumination devices or imagers, which may be behind the dome. The dome may be forward projecting and may have a convex shape. The field of view of the imager may be for example forward looking. Illumination element(s) and a receiving unit or imager may be disposed behind a single optical window, which for example may enable obtaining images free of backscatter and stray light. The convex shape of the dome may be defined such that it may have a shape having an isolated area. At least one illumination element and at least one receiving unit may be geometrically positioned (for example in the isolated area) such that rays from the illumination elements, some of which are internally reflected from the internal and/or external surface of the optical window, will not be incident on the receiving unit.

20 Claims, 9 Drawing Sheets

U.S. PATENT DOCUMENTS

| | | | |
|---|---|---|---|
| 3,683,389 A | 8/1972 | Hollis |
| 3,745,325 A | 7/1973 | Harvey |
| 3,971,362 A | 7/1976 | Pope et al. |
| 4,005,287 A | 1/1977 | Cook |
| 4,017,163 A | 4/1977 | Glass |
| 4,027,510 A | 6/1977 | Hiltebrandt |
| 4,177,800 A | 12/1979 | Enger |
| 4,198,960 A | 4/1980 | Utsugi |
| 4,217,045 A | 8/1980 | Ziskind |
| 4,234,912 A | 11/1980 | Barnes et al. |
| 4,239,040 A | 12/1980 | Hosoya et al. |
| 4,278,077 A | 7/1981 | Mizumoto |
| 4,439,197 A | 3/1984 | Honda et al. |
| 4,491,865 A | 1/1985 | Danna et al. |
| 4,596,050 A | 6/1986 | Rogers |
| 4,646,724 A | 3/1987 | Sato et al. |
| 4,689,621 A | 8/1987 | Kleinberg |
| 4,735,214 A | 4/1988 | Berman |
| 4,741,327 A | 5/1988 | Yabe |
| 4,819,620 A | 4/1989 | Okutsu |
| 4,844,076 A | 7/1989 | Lesho et al. |
| 4,917,097 A | 4/1990 | Proudian et al. |
| 4,936,823 A | 6/1990 | Colvin et al. |
| 4,951,135 A | 8/1990 | Sasagawa et al. |
| 5,010,412 A | 4/1991 | Garriss |
| 5,042,486 A | 8/1991 | Pfeiler et al. |
| 5,166,787 A | 11/1992 | Irion |
| 5,187,572 A | 2/1993 | Nakamura et al. |
| 5,217,449 A | 6/1993 | Yuda et al. |
| 5,222,477 A | 6/1993 | Lia |
| 5,267,033 A | 11/1993 | Hoshino |
| 5,279,607 A | 1/1994 | Schentag et al. |
| 5,335,662 A | 8/1994 | Kimura et al. |
| 5,368,027 A | 11/1994 | Lubbers et al. |
| 5,373,840 A | 12/1994 | Knighton |
| 5,395,366 A | 3/1995 | D'Andrea et al. |
| 5,429,132 A | 7/1995 | Guy et al. |
| 5,489,256 A | 2/1996 | Adair |
| 5,495,114 A | 2/1996 | Adair |
| 5,603,687 A | 2/1997 | Hori et al. |
| 5,604,531 A | 2/1997 | Iddan et al. |
| 5,653,677 A | 8/1997 | Okada et al. |
| 5,662,587 A | 9/1997 | Grundfest et al. |
| 5,681,260 A * | 10/1997 | Ueda et al. | 600/114 |
| 5,697,384 A | 12/1997 | Miyawaki et al. |
| 5,718,663 A | 2/1998 | Wulfsberg |
| 5,745,833 A | 4/1998 | Abe et al. |
| 5,764,274 A | 6/1998 | Sousa et al. |
| 5,819,736 A | 10/1998 | Avny et al. |
| 5,833,603 A | 11/1998 | Kovacs et al. |
| 5,840,014 A | 11/1998 | Miyano et al. |
| 5,993,378 A | 11/1999 | Lemelson |
| 6,240,312 B1 | 5/2001 | Alfano et al. |
| 6,416,181 B1 | 7/2002 | Kessler et al. |
| 6,428,469 B1 | 8/2002 | Iddan et al. |
| 6,511,182 B1 | 1/2003 | Agostinelli et al. |
| 6,612,701 B2 | 9/2003 | Westort et al. |
| 6,632,171 B2 | 10/2003 | Iddan et al. |
| 6,632,175 B1 | 10/2003 | Marshall |
| 6,709,387 B1 | 3/2004 | Glukhovsky et al. |
| 6,764,440 B2 | 7/2004 | Iddan et al. |
| 6,836,377 B1 | 12/2004 | Kislev et al. |
| 6,918,872 B2 * | 7/2005 | Yokoi et al. | 600/129 |
| 6,934,093 B2 | 8/2005 | Kislev et al. |
| 6,984,205 B2 * | 1/2006 | Gazdzinski | 600/160 |
| 7,009,634 B2 | 3/2006 | Iddan et al. |
| 7,327,525 B2 | 2/2008 | Kislev et al. |
| 2001/0017649 A1 | 8/2001 | Yaron |
| 2001/0035902 A1 | 11/2001 | Iddan et al. |
| 2001/0051766 A1 | 12/2001 | Gazdzinski |
| 2002/0103417 A1 | 8/2002 | Gazdzinski |
| 2002/0198439 A1 | 12/2002 | Mizuno |
| 2003/0018280 A1 | 1/2003 | Lewkowicz et al. |
| 2003/0020810 A1 | 1/2003 | Takizawa et al. |
| 2003/0085994 A1 | 5/2003 | Fujita et al. |
| 2003/0139647 A1 | 7/2003 | Raz et al. |
| 2003/0158503 A1 * | 8/2003 | Matsumoto | 600/593 |
| 2003/0167000 A1 | 9/2003 | Mullick et al. |
| 2003/0171468 A1 | 9/2003 | Nishimura et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0208107 A1 | 11/2003 | Refael |
| 2004/0073087 A1 | 4/2004 | Glukhovsky et al. |
| 2004/0171914 A1 | 9/2004 | Avni |
| 2005/0068416 A1 | 3/2005 | Glukhovsky et al. |
| 2005/0185299 A1 | 8/2005 | Kislev et al. |
| 2007/0002135 A1 | 1/2007 | Glukhovsky |

FOREIGN PATENT DOCUMENTS

| | | |
|---|---|---|
| DE | 2929429 | 2/1980 |
| DE | 34 40 177 | 5/1986 |
| DE | 34 40 177 | 5/1989 |
| DE | 3928515 | 6/1990 |
| DE | 9016829 | 2/1991 |
| EP | 0667115 | 8/1995 |
| EP | 0 677 0272 | 10/1995 |
| EP | 0 941 691 | 9/1999 |
| FR | 2723215 | 2/1996 |
| GB | 2291980 | 2/1996 |
| JP | 57-45833 | 3/1982 |
| JP | 63-200115 | 8/1988 |
| JP | 63200115 | 8/1988 |
| JP | 6142081 | 5/1991 |
| JP | 3264037 | 11/1991 |
| JP | 03264037 A | 11/1991 |
| JP | 3289779 | 12/1991 |
| JP | 4109927 | 4/1992 |
| JP | 04-144533 | 5/1992 |
| JP | 1992-144533 | 5/1992 |
| JP | 4180736 | 6/1992 |
| JP | 5015515 | 1/1993 |
| JP | 6063051 | 3/1994 |
| JP | 6114037 | 4/1994 |
| JP | 6285044 | 10/1994 |
| JP | 111985 | 5/1995 |
| JP | 7289504 | 11/1995 |
| JP | 08-248326 | 9/1996 |
| JP | 11-142933 | 5/1999 |
| JP | 2001-046358 | 2/2001 |
| JP | 2001-091860 | 4/2001 |
| JP | 2001-095755 | 4/2001 |
| JP | 2001-095756 | 4/2001 |
| JP | 2001-104241 | 4/2001 |
| JP | 2001-104242 | 4/2001 |
| JP | 2001-104243 | 4/2001 |
| JP | 2001-104244 | 4/2001 |
| JP | 2001-104287 | 4/2001 |
| JP | 2001-137182 | 5/2001 |
| JP | 2001-170002 | 6/2001 |
| JP | 2001-174713 | 6/2001 |
| JP | 2001-224551 | 8/2001 |
| JP | 2001-224552 | 8/2001 |
| JP | 2001-224553 | 8/2001 |
| JP | 2001-231744 | 8/2001 |
| JP | 2001-245844 | 9/2001 |
| JP | 5015515 | 1/2003 |
| JP | 2005-003828 | 1/2005 |
| WO | WO 98/11816 | 3/1998 |
| WO | WO 00/22975 | 4/2000 |
| WO | WO 00/76391 A1 | 12/2000 |
| WO | WO 01/08548 | 2/2001 |
| WO | WO 01/65995 | 9/2001 |

| WO | WO 02/055126 | 7/2002 |
| WO | WO 02/095351 | 11/2002 |
| WO | WO 03-011103 | 2/2003 |
| WO | WO 2004/035106 | 4/2004 |

OTHER PUBLICATIONS

The Radio Pill, Rowlands et al British Communications and Electronics, Aug. 1960 pp. 598-601.

Wellesley company sends body montiors into space—Crum, Apr. 1998.

Wireless transmission of a color television moving image from the stomach using a miniature CCD camera, light source and microwave transmitter Swain CP Gong F Mills TN Gastrointest Endosc 1997;45:AB40.

Manual of Photogrammetry Thompson (Ed) Third Edition, Volume Two American Society of Photogrammetry 1966.

BBC News Online—"Pill camera to 'broadcast from the gut'" Feb. 21, 2000, www news bbc co uk.

Katgraber F, Glenewinkel F, Fischler S Int. J Legal Med 1998; 111(3) 154-6.

European Search Report of European Application 00937157 6. dated Feb. 3, 2004.

"An endogastric capsule for measuring tumor markers in gsaric juice: an evaluation of the safety and efficacy of a new diagnostic tool" Muretto et al., Jan. 2003.

Electronic Sputnik Capsule Against Parasites—Turner, 2001.

Evans et al., Studies of the Human Gastro-Intestinal Tract in the Ambulatory Subject Using the Pressure Sensitive Radiotelemetry Capsule.

Evaluation of the Heidelberg pH Capsule, Yarbrough, et al., The American Journal of Surgery, vol. 117, Feb. 1969, pp. 185-192.

European Office Action for Application No. 0937157.6 dated Nov. 9, 2004.

European Search Report for Application No. 05026710.3 dated Jan. 31, 2006.

European Office Action for Application No. 05026710.3 dated Nov. 16, 2006.

European Search Report for Application No. 06022666.9 dated Dec. 12, 2006.

European Search Report for Application No. EP 07001478 mailed Apr. 10, 2007.

International Search Report for Application No. PCT/IL00/00349 Mailed Nov. 27, 2000.

Localization of a wireless capsule endoscope in the GI Tract, Gastrointestinal Endoscopy 2001;53:AB126.

Nam, et al., "A method for Position Detection of the wireless capsule endoscopes Module Using the Solution of Nonlinear Simultaneous Equations", Sensors Conference 2002, p. 377.

Notice of Allowance for U.S. Appl. No. 11/291,906 mailed May 2, 2007.

Office Action for U.S. Appl. No. 10/009,837 dated Oct. 2, 2003.

Office Action for U.S. Appl. No. 10/009,837 dated Apr. 30, 2004.

Office Action for U.S. Appl. No. 10/879,276 dated Dec. 14, 2004.

Office Action for U.S. Appl. No. 11/115,320 mailed Mar. 30, 2006.

Office Action for U.S. Appl. No. 11/115,320 dated Oct. 13, 2006.

Office Action for U.S. Appl. No. 10/879,483 mailed Mar. 20, 2007.

Office Action for U.S. Appl. No. 11/115,320 mailed Apr. 30, 2007.

Japanese Office Action for Application No. 2001-502738 dated Aug. 2, 2005.

Japanese Office Action for Application No. 2005-155953 dated Aug. 2, 2005.

Robots for the future—Shin-ichi, et al.

The Heidelburg pH Capsule System Telemetric Fasting Gastric Analysis.

Transit times for the Capsule Endoscope, Gastrointestinal Endoscopy 2001; 53:AB122.

Video Camera to "TAKE"—RF System Lab, Dec. 25, 2001.

Wang, et al., "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.

Weitschies, et al., Magnetic marker monitoring of disintegrating capsules, European Journal of Pharmaceutical Sciences 13, 411-416, 2001.

Written Opinion for Application No. PCT/IL00/00349 mailed Apr. 13, 2001.

W. Weitschies, R. Kotitz, D. Cordin, L. Trahms, High-Resolution Monitoring of the Gastrointestinal Transit of a Magnetically Marked Capsule, (1997), Journal of Pharmaceutical Sciences, vol. 86, No. 11, pp. 1218-1222.

www.rfnorkia.com—NORIKA3, Dec. 24, 2001.

www.middleeasthealthmag.com—Review proves the value of computers. 2001.

BBC News Online-"Pill camera to 'broadcast from the gut'", Feb. 21, 2000 www.news.bbc.co.uk.

Katgraber F, Glenewinkel F, Fischler S, Int. J. Legal Med. 1998; 111(3):154-6.

Manual Photogrammetry, Thompson (Ed.), Third Edition, vol. Two, American Society of Photogrammetry, 1966.

Rowlands et al., The Radio Pill, British Communications and Electronics, Aug. 1960, pp. 598-601.

Wellesley Company Sends Body Monitors into Space—Crum, Apr. 1998.

Wireless Transmission of a Color Television Moving Image from the Stomach using a miniature CCD camera, Light Source and Microwave Transmitter, Swain CP, Gong F, Mills TN, Gastrointest Endosc 1997; 45:AB40.

Office Action for U.S. Appl. No. 10/879,483 mailed on Oct. 31, 2008.

Office Action for U.S. Appl. No. 10/879,483 dated Apr. 29, 2009.

Office Action for U.S. Appl. No. 10/879,483, issued on Oct. 23, 2009.

Evans et al., Studies of the Human Gastro-Intestinal Tract in the Ambulatory Subject Using the Pressure Sensitive Radiotelemetry Capsule, 1989.

Final Office Action, issued Apr. 27, 2010, for U.S. Appl. No. 10/879,483.

* cited by examiner

IN-VIVO IMAGING DEVICE, OPTICAL SYSTEM AND METHOD

CROSS REFERENCE TO RELATED APPLICATIONS

This application is a continuation-in-part of U.S. application Ser. No. 10/879,483 filed on 30 Jun. 2004, entitled "In-Vivo Imaging Device, Optical System and Method" which in turn is a continuation-in-part of U.S. application Ser. No. 10/009,837 filed on 22 Aug. 2002, entitled "An Optical System", now U.S. Pat. No. 6,836,377 which is a national phase application of International Application PCT/IL00/00349 filed 15 Jun. 2000, and a continuation-in-part of U.S. application Ser. No. 10/478,252 filed on 20 Nov. 2003, entitled "A Method for In Vivo Imaging of an Unmodified Gastrointestinal Tract", which is a national phase application of International Application PCT/IL02/00391 filed 20 May 2002, all of which are incorporated in their entirety by reference herein. International Application PCT/IL00/00349 filed 15 Jun. 2000 claims benefit from Israeli Patent Application No. IL 130486 filed 15 Jun. 1999. International Application PCT/IL02/00391 filed 20 May 2002claims benefit from Israeli Patent Application No. IL 143258 filed 20 May 2002.

FIELD OF THE INVENTION

The present invention relates to an in-vivo device for imaging; more specifically, to optical systems for such devices and methods for their use, and to in vivo imaging of lumens such as the gastrointestinal tract in unmodified conditions.

BACKGROUND OF THE INVENTION

An optical system for illuminating and viewing a target, which may include for example a source of illumination of the target and an imager or other device for receiving the light remitted from the target, may be defined by or analyzed in light of, for example, an illumination axis and optical axis that may converge at the target.

Such an optical system may be as simple as an operator of an illumination source viewing a target, wherein the operator embodies the imager, and is the unit receiving the light remitted from the target. An example of such an optical system is an operator of a vehicle inside the vehicle and looking out at an illuminated target such as a road or tunnel walls.

Other optical systems may include other components such as automated processors as imaging devices receiving the light remitted from a viewed target. Examples of such optical systems may be found in diagnostic apparatuses such as endoscope devices. The endoscopes described in the art may include, for example an image pickup element and an illuminating element for illuminating an examined target, and other components For some optical systems it may be advantageous to have the illuminating element and receiving element contained within a single compartment, for example behind a single optical window and or viewing window.

In devices typically used to view the gastrointestinal tract, such as endoscopes, when the device may be inserted into the intestine the field of illumination may be obscured by folds of the intestine wall collapsing on the tip of the endoscope. It may be difficult to push devices through the intestines or other body lumens without potentially causing a lesion or tear of the body lumen wall. This and other problems may be solved by insufflating air in the intestine. Air insufflation may inflate the intestinal walls, flatten the folds that may be naturally present in the intestine wall, and may remove potential obstruction from both the illumination source(s) and from the imager.

Air insufflation of the intestine may change the normal physiological conditions of the intestine. Air insufflation may modify these conditions.

SUMMARY OF THE INVENTION

Embodiments of the present invention may include an in-vivo device, an optical system, and a method for viewing in-vivo sites.

A dome or cover may cover an end of the device, protecting optical elements such as illumination devices or imagers, which may be behind the dome.

In some embodiments, the device may illuminate and view a target in which device an illumination element and a receiving unit are disposed behind a single optical window or dome. According to one embodiment of the present invention, the optical dome may have a shape that may define a backscatter area and/or an isolated area, e.g a confined area where backscatter may be incident, wherein illumination element is positioned and a central area wherein a receiving element is positioned such that light from an illumination element originating from within the focal area when reflected off the optical dome may not be incident on said central area. According to one embodiment, the optical dome may have a shape of a section of a flattened/deformed ellipsoid. According to some embodiment of the present invention, images may be obtained with, for example, reduced or no backscatter, or stray light.

An optical system according to an embodiment of the present invention may include at least one illumination element and at least one receiving unit, both disposed behind a single optical window. According to some embodiments of the present invention, the receiving unit may include a baffle surrounding an imager that may have an aperture In some embodiments, the optical window may be configured such that it may define a shape having at least one focal area. At least one illumination element and at least one receiving unit may be geometrically positioned (for example in the focal area) such that, when illuminating, rays from the illumination elements, some of which are internally reflected from the internal and/or external surface of the optical window, will not be incident on the receiving unit.

BRIEF DESCRIPTION OF THE DRAWINGS

The present invention will be understood and appreciated more fully from the following detailed description taken in conjunction with the figures in which.

Figure 1:
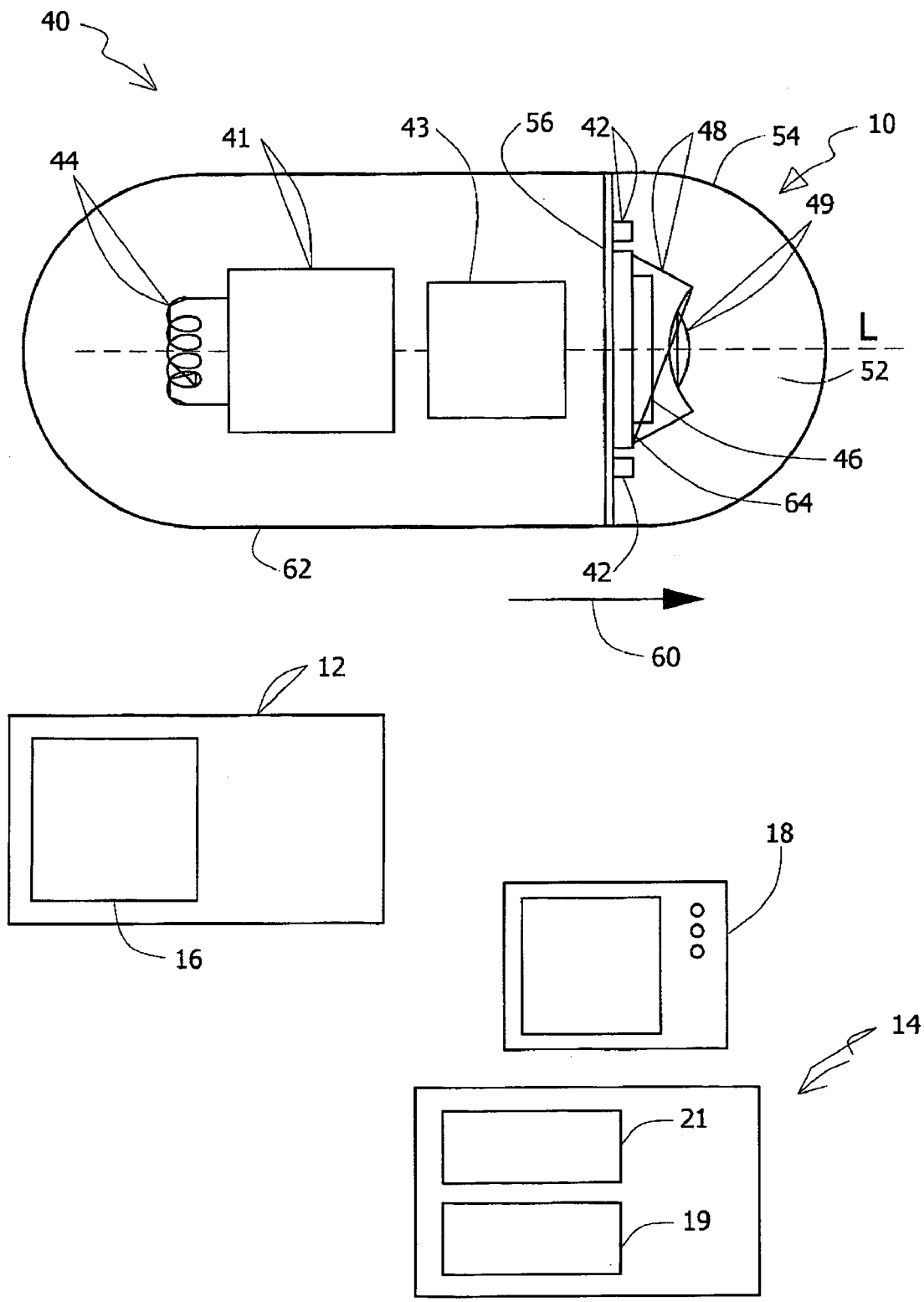
FIG. 1 is a schematic diagram of a device and system according to embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

It will be appreciated that the terms "receiving unit" and "imaging unit" relate to any unit suitable for receiving, processing or further transmitting illumination rays remitted from a target or data derived from these rays. For example, an imager or camera, such as a Charge Coupled Device (CCD) camera or imager or a Complementary Metal Oxide Semiconductor (CMOS) imager or camera may be used; other suitable receiving or imaging units may be used.

Embodiments of the present invention include an optical system which may geometrically position both illumination elements and units for receiving light behind a single optical window, viewing window, dome, etc., such that internally reflected (e.g., by refraction) light from the optical window may not be incident on the receiving unit.

An optical window having a shape having focal points (for example, an ellipse) has the optical property that light rays emitted from one focal point of the shape, which are internally reflected, may be propagated to the second focal point. In a three dimensional shape (such as a section of an ellipsoid) light rays emitted from a point on a focal curve, which are internally reflected, may be propagated to another point on the focal curve.

For example, in the field of arc lamp systems this property may be used to collect energy and/or reflected light efficiently. For example in Model A-1010 and A-1010B lamp housings provided by Photon Technology International of New Jersey, USA, an arc source may be located at and/or substantially near a foci of an ellipsoid reflector and the radiation may be reflected to another foci. Energy may be collected efficiently since the light may be brought to a focus by reflection rather than by refraction (through a lens) such that there may be no loss due to absorption or lens surface back reflection.

In the optical system of some embodiments of the present invention the illumination elements and receiving unit, e.g. an imager may be positioned within an optical dome such that illumination rays from the illumination source that may be internally reflected from the inner and/or outer surface of optical window may not be incident and/or may not be substantially incident on the imager and/or other light receiving device. For example, the illumination sources may be positioned on and/or near focal points and the imager's position may not coincide with the focal points, thus substantially ensuring that internally reflected light from the inner and/or outer surface of optical window may be propagated to focal points and not substantially received by the receiving unit, for example the imager. Other configurations may be possible.

Some embodiments of the present invention may include imaging devices that may include a configuration which may allow imaging of an un-modified or un-insufflated lumen; in some contexts and with some uses such techniques may be referred to as "airless endoscopy".

Various embodiments of the invention need not include all the aspects discussed herein. For example, an in-vivo imaging device (e.g., an endoscope, a capsule, etc) may include a protruding dome, but may not include an arrangement for avoiding backscatter as may be disclosed herein.

A system according to some embodiments of the invention may include an in-vivo sensing device transmitting information (e.g., images or other data) to a data receiver and/or recorder possibly close to or worn on a subject. A data receiver and/or recorder may of course take other suitable configurations. The data receiver and/or recorder may transfer the received information to a larger computing device, such as a workstation or personal computer, where the data may be further analyzed, stored, and/or displayed to a user. In other embodiments, each of the various components need not be required and or may be housed in alternate configurations; for example, an internal device may transmit or otherwise transfer (e.g, by wire) information directly to a viewing or processing system. In another example, the data receiver or workstation may transmit or otherwise transfer information to the in-vivo device. While in one embodiment the device may be an autonomous capsule, other configurations, such as an endoscope or trocar may be used Reference is made to FIG. 1, which is a schematic diagram of a device and system according to one embodiment of the present invention In one embodiment, the system may comprise an in-vivo imaging device, such as for example a device 40 which may, for example, be capsule shaped, an optical system 10 including, for example, optical window 54, one or more lens(es) 49, lens holder, baffle, or separator 48, an imager 46 or other receiving unit, one or more illumination source(s) 42, and one or more power source(s) 43. Power source(s) 43 may be, for example, a suitable battery, but in further embodiments may be other devices, such as a unit for receiving power from an external source. Optical system 10 may be described in more detail herein. Optical window 54 may typically define a space 52 behind which may sit optical components such as imager 46, baffle 48, one or more lenses 49, and one or more illumination source(s) 42. For example, if the empty areas inside device 40 include common air rather than a specialized isolated gas, space 52 may be an air space. Window 54 may be protective optical window, preferably made of plastic such as thermoplastic polyurethane resins, polymethyl methacrylate, cyclic olefin copolymer or other suitable material such as other plastics, glass, etc. Baffle or separator 48 may provide additional functionality, such as holding other components. For example baffle 48 may act as a lens holder. Baffle or separator 48 may help to optically isolate imager 46 and illumination source(s) 42. Typically, the imager 46 images via optical window 54 and illumination source(s) 42 illuminate via optical window 54. Baffle 48 may include an aperture through which light reflected from, for example, an object 15 may be received. Device 40 may include a transmitter 41 (typically operating wirelessly via radio waves), and an antenna 44, for transmitting images and possibly other information to, for example, a receiving device 12. Other types of transmitters and transmission methods may be used; for example, in an endoscope application, wire or other transmission may be used.

Imager 46 may be fixed or otherwise attached to a substrate such as, for example, circuit board 64 or directly positioned onto a substrate 56. In other embodiments, circuit board 64 may be further attached to a substrate 56, which may for example support illumination source(s) 42 (which may be supported by its/their own substrate or circuit board, which may be supported by or integrated with substrate 56) and which may define a viewing direction 60 of device 40. In other embodiments, illumination source(s) may be positioned on a different plane than, for example, imager 46. For example, illumination source(s) 42 may be position on the plane and/or at a height that corresponds to an opening, for example an aperture of the baffle 48. Other suitably defined heights for illumination source(s) as compared to the imager 46 may be used.

Optical window 54 may form space 52, so that illumination source(s), imager 46, and/or baffle 48 may be recessed behind optical window 54. In one embodiment, imager 46 may be positioned within space 52 and at least some imaging portions of the imager 46 may not be in direct contact with the optical window 54 but rather may be recessed from optical window 54 and substantially within the space 52. Circuit board 64 may be any suitable substrate, such as a circuit board, a plastic sheet or plate, etc. The imaging device may be similar to, for example, embodiments described in U.S. Pat. No. 5,604,531 to Iddan et al., and/or to embodiments described in U.S. Application Publication No US20010035902 published on Nov. 1, 2001, both of which are incorporated herein by reference in their entirety, but in alternate embodiments there may be other types of imaging devices. In one embodiment, an imaging device may include more than one image sensor. For example, an additional optical system may be included in a direction opposite viewing direction 60, to form for example a double ended viewing device. Other configurations for including more than one imager 46 in device 40 and/or more than one viewing direction may be implemented. Device 40, and other devices disclosed herein, may be used to view lumens such as the gastrointestinal tract in a natural state and/or in an unmodified form, not using or requiring techniques such as insulation.

Typically, located outside the patient's body in one or more locations may be an image receiver 12, a data processor 14, and an image monitor 18. Image receiver 12 may include an image receiver storage unit 16. Data processor 14 may include a processor and/or CPU 19 and a storage unit 21.

Optical window 54 may be in one embodiment convex or substantially convex and smooth, and may project outward from the main body and/or housing 62 of device 40 in a "forward" (and/or viewing) direction 60, although note that "forward" is a relative term, as in some embodiments in use the imaging section of device 40 may either lead or follow the rest of the device 40 as it traverses a body lumen. For example, the device 40 may, depending on circumstance, traverse a lumen such that the imager 46 may face the substantially upstream and/or downstream direction, as device 40 may be designed so that there may be two possible directions of travel, both substantially parallel to the axis L of device 40. The direction of travel need not be parallel to the longitudinal axis L, and other configurations (e.g., spherical) may be used. In an embodiment where the device 40 has one or two possible directions of travel (e.g., downstream, or downstream and upstream), the forward end may be defined as being at the end of the device in which the device travels, or one of such ends. In one embodiment, the field of view of the imager 46 via the optical system may be along the longitudinal axis L and towards the "front" end; objects generally beyond the "front" end, such as target or object 15, are imaged. Optical window 54 may be ellipsoid shaped or substantially ellipsoid shape, but may include other non-elipsoid convex shapes.

Optical window 54 may typically be transparent and/or substantially transparent, or may include a transparent window or transparent portion. Optical window 54 may typically provide one uninterrupted field of view for optical components. The optical dome 54 may in some embodiments project from the main body 62 of the device (possibly in a smooth contoured manner, and may be integral with the main body 62), and thus may lead or follow the device through a lumen, depending on the direction of travel. The optical dome 54 may be preferably made of plastic, glass as may be described herein or other suitable material. Typically, the area to be viewed may be illuminated and viewed through the optical dome 54, and thus optical components such as the imager 46 and illumination elements 42 may be behind the dome 54, within the device 40. Typically, optical window 54 in combination with the main body and/or housing 62 may provide a relatively smooth and streamlined body for traversing through body lumens. Typically, at least one end of the device 40 may be substantially convex; for example optical window 54 may be considered a convex forward projecting or protruding end of device 40. The window 54 may typically protrude relative to a direction of travel of the device 40. The device 40 may typically collect images of objects which may be located generally forward of the forward end of the device 40 (or backward if the device 40 may be facing upstream and progressing downstream), typically up to a 140 degree angle of view although other angles may be used.

Typically, the optical window 54 or the optical dome is one piece of plastic or glass as may be described herein or other suitable material, which may be fixed to the overall device and may be disposed of with the device. However, in other embodiments, the optical window or dome may be more than one unit, and need not be a separate unit from the rest of the shell for the device. In addition, in one embodiment, since protective optical window 54 is a single and complete unit, it is easily disposable, and can be smoothly transported through different passes through the digestive tract. This may contribute to the sterile and facile use of a diagnostic device.

Main body 62 may be in some embodiments the tube of an endoscope or trocar, and thus may extend further rearward than may be depicted in the device 40 of FIG. 1. Further, more than one optical system may be included in a device such as device 40. For example, a device similar to embodiments described in U.S. application Ser. No. 10/046,541 filed on 16 Jan. 2002 which is, incorporated by reference in its entirety, may include optical systems as described herein.

Imager 46 may include, for example, a CCD camera or imager, a CMOS camera or imager, a digital camera, a still camera, a video camera, or other suitable one or more imagers, cameras, receiving units or image acquisition components.

Device 40 may typically be or may typically include an autonomous swallowable capsule, which may be self contained, but device 40 may have other shapes and need not be swallowable or autonomous (e.g., device 40 may have other configurations, such as that of an endoscope or trocar). In one embodiment, device 40 may be shaped such that its eccentricity may be equal to or larger than zero and smaller than 1. Device 40 may be in the form of a capsule or other unit where all the components may be substantially contained within a container, housing, or shell, and where device 40 may not require any wires or cables to, for example, receive power or transmit information and may be autonomous. In one embodiment, all of the components may be sealed within the device body (the body or shell may include more than one piece); for example, an imager, illumination units, power units, and transmitting and control units, may all be sealed within the device body. Device 40 may communicate with an external receiving and display system to provide display of data, control, or other functions. For example, power may be provided by an internal battery or a wireless receiving system. Other embodiments may have other configurations and capabilities For example, components may be distributed over multiple sites or units. Control information may be received from an external source.

Transmitter 41 may include control capability for, for example controlling the various operations of device 40, although control capability or one or more aspects of control may be included in a separate component. In some embodiments of the present invention, transmitter 41 may typically be an ASIC (application specific integrated circuit), but may be of other constructions; for example, transmitter 41 may be a processor executing instructions. Device 40 may include a processing unit separate from transmitter 41 that may, for example, contain or process instructions.

Typically, located outside the patient's body in one or more locations may be an image receiver 12, a data processor 14, and an image monitor 18. Image receiver 12 may typically include an antenna or antenna array and an image receiver storage unit 16. Data processor 14 may include a processor 19 and a storage unit 21. Image monitor 18 may display, inter alia, images recorded by, for example, device 40. Typically, data processor 14 and monitor 18 may be part of a personal computer or workstation, which may include standard components such as a processor 19, a memory, a disk drive, and input-output devices, although alternate configurations are possible. Data processor 14 may typically, as part of its functionality, act as a controller controlling the display of the images. Image monitor 18 may typically be a conventional video display, but may, in addition, be any other device capable of providing images or other data and may be of any size monitor including large projection size monitors. The image monitor 18 may present the image data, typically in the form of still and/or streaming image frames, and in addition may present other information. In an exemplary embodiment, the various categories of information may be displayed in windows. Other displaying formats may be used. In other embodiments of the present invention, one or more of the components included in receiver 12 and data processor and/or workstation 14 may be packaged in alternate configuration and may be or may be included in a portable or stationary device, package, and/or housing.

In operation, imager 46 may capture images and may send data representing the images to transmitter 41, which may transmit data to image receiver 12 using, for example, electromagnetic radio waves. Image receiver 12 may transfer the image data to image receiver storage unit 16. After a certain period of time of data collection, the image data stored in storage unit 16 may be transferred to the data processor 14 or the data processor storage unit 21 For example, the image receiver 12 or image receiver storage unit 16 may be taken off the patient's body and may be connected to a personal computer or workstation that may include the data processor 14 via a standard data link, e.g., a serial, parallel, USB, or wireless interface. According to one embodiment the image data may then be transferred from the image receiver storage unit 16 to data processor storage unit 21. Data processor 14, including possibly dedicated software, may analyze the data and provide the analyzed data to the image monitor 18, where a user views the image data. Other configurations allow for real time viewing. Further, other methods of recording, transmitting, storing and viewing images recorded by imager 46 may be used.

Figure 2:
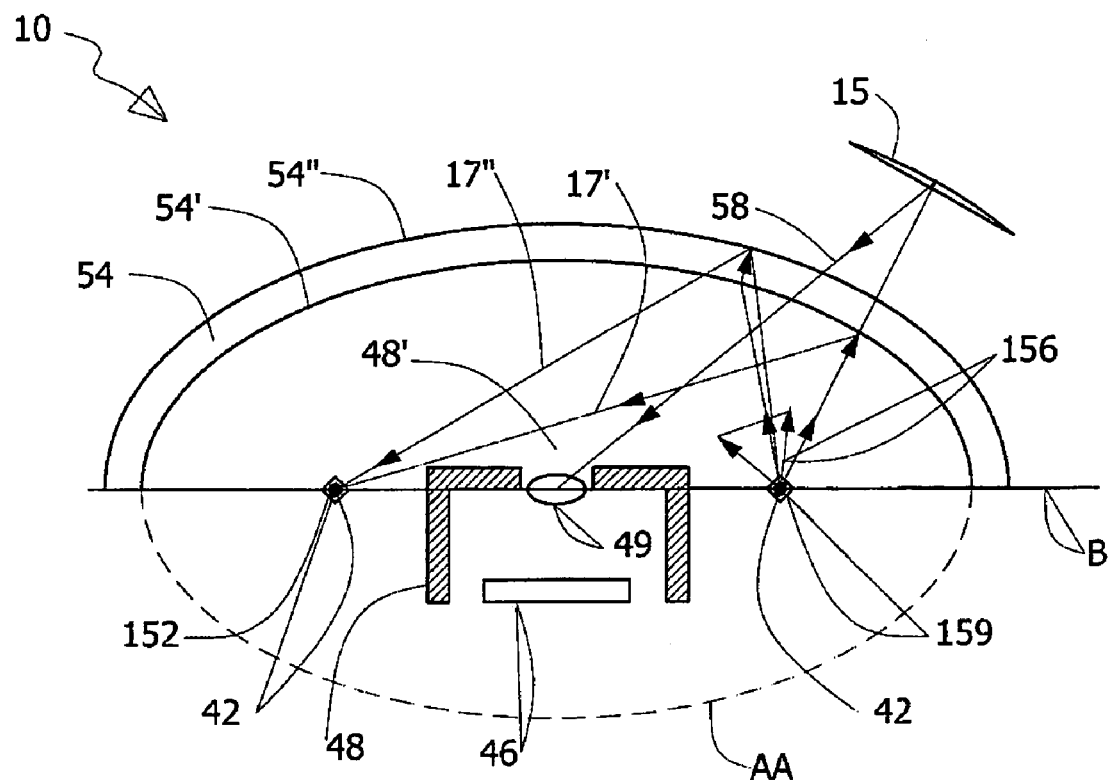
FIG. 2 is a schematic illustration of an optical system according to one embodiment of the present invention.

Reference is now made to FIG. 2, a schematic two dimensional presentation of an optical system according to an embodiment of the present invention Referring to FIG. 2, optical system generally referenced as 10 may be included in, for example, device 40 of FIG. 1, but may be included in other suitable devices, such as an endoscope, trocar, or other invivo imaging device. Optical system 10 may include, for example, illumination source(s) 42, imager 46, and one or more lenses disposed and possibly recessed behind an optical window 54, for viewing, for example, a target or object 15. One, two, or more than two illumination sources may be used. Optical window 54 may have an inner surface 54' configured such that a shape defined by it and by broken line AA may have an axis of symmetry B and, when viewed in cross section, may have two focal points 159 and 152. Multiple focal points form a focal curve, ring, or circle when viewed in three dimensions, for example in FIG. 3, a ring of focal points including focal points 159 and 152 may form a circle, ring or other shape lying in a focal plane. Illumination source(s) 42, which may include one, two or more than two light sources, may be positioned on or substantially near or around focal point 159 or on a focal curve and possibly other focal points and an opening or aperture 48' and/or one or more lenses 49 may be positioned, for example, on the axis of symmetry B not coinciding with either focal point 159 or 152 or other focal points or not lying on the focal curve. In some embodiments of the present invention, an imager 46 and or lens 49 may be positioned on a plane other than the plane defined by the focal curve, for example a plane below the axis of symmetry B.

The course of light rays emitted from illumination sources 42 will be followed as an example of the behavior of illumination rays in the optical system according to an embodiment of the invention. Light 156 may be emitted from an illumination source 42 (which element's position coincides with a focal point 159) for illuminating target 15. A percent of the light (represented by ray 17') may be internally reflected (typically via refraction) from the optical window 54 internal surface 54' and may be propagated to, for example, the second focal point 152. A certain percent of the light (represented by ray 17") may be internally reflected (typically via refraction) from the optical window 54 external surface 54" and may be propagated, for example, to the second focal point 152 or in the vicinity and/or area substantially near focal point 152. A percent of the light 156 (represented by ray 58) may be incident on target 15 (e.g., an object or area in-vivo) and may be reflected from target 15 and received through aperture 48' and/or lens 49 by imager 46

Thus, internally reflected light rays (such as ray 17' and 17") may be propagated to areas outside aperture 48' that may direct light to the imager 46. Light reflected from the external surface 54" may be bent and may be reflected to an area near and or substantially near the focal curve and substantially away from aperture 48' and/or lens 49.

Imager 46 may also be unexposed to direct illumination from illumination sources 42; direct light from the illumination sources 42 may generally not be incident on the imager 46. In some embodiments of the present invention, the illumination source(s) 42 may be placed above (where above is a relative term when the device is viewed as in FIG. 2) imager 46 and imager 46 may be protected by a baffle 48 substantially surrounding imager 46. Illumination sources 42 may be positioned in or may illuminate light rays 156 in, for example, a circular band that may be, for example, tangent to line B. In such a case, if imager 46 is positioned on line B it may not receive substantially any direct illumination rays, and/or stray light from illumination sources 42. Alternatively, imager 46 may be concealed in a niche, or surrounded or protected by for example a baffle 48 or other structure, to avoid receiving direct illumination rays from illumination sources 42.

Thus, geometric positioning of the components of the system ensures that no backscatter or minimized backscatter, such as ray 17' and 17", and no direct light or minimized direct light may be received by imager 46, one or more lenses 49 directing light to imager 46, or through aperture 48' and only incident light, such as ray 58, may be received by and/or incident on imager 46.

In actuality, the optical window 54 is a three dimensional shape. A schematic three dimensional representation of the optical system 10 of FIG. 2, according to one embodiment, is shown in FIG. 3.

Figure 3:
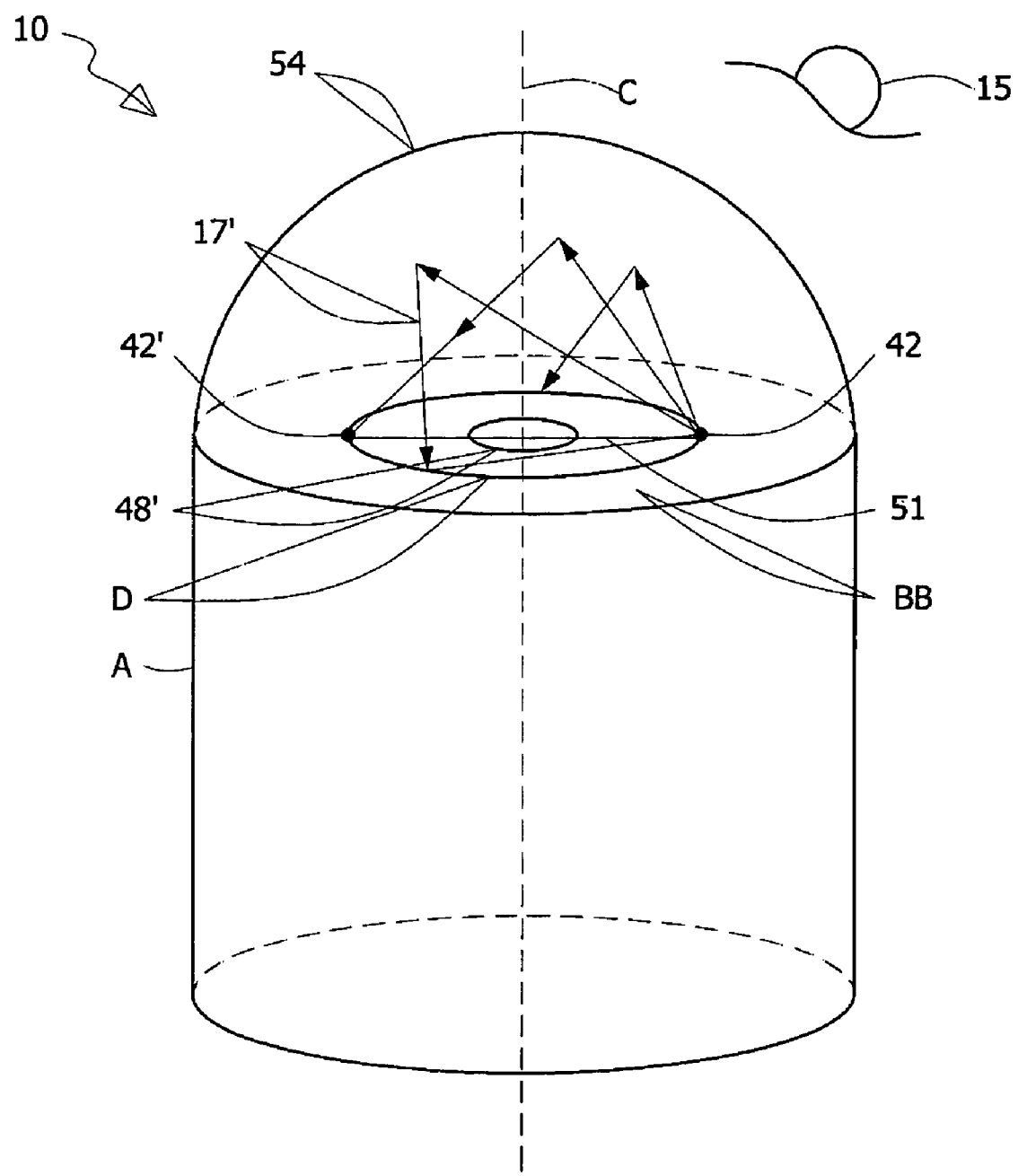
FIG. 3 is a schematic illustration of an optical system with a focal curve defined by the geometry of a viewing dome according to an embodiment of the present invention.

In optical system 10 shown in FIG. 3, plane BB including line B from FIG. 2 is shown. Axis C may be perpendicular to plane BB. The shape on plane BB which may be defined by optical window 54, may encompass focal curve D. In other embodiments other arrangements and shapes for focal points, a focal curve, and a plane on which a focal curve lies, may be used. A light ray 17' that may be internally reflected (typically via refraction) from the optical window 54 internal surface may be propagated, for example, to a point on the focal curve D.

One or more illumination elements, such as 42 and 42', may be positioned on focal curve D to, for example, help enable a uniform spatial illumination or to produce other results, though it should be appreciated that any suitable number of illuminating elements including a single illumination source may be used according to specific requirements of the system.

In the arrangement shown, aperture 48' and/or other suitable points of entrance of light rays toward imager 46 may be positioned at a point which is on, or in the vicinity of, axis C, for example at an equal distance from both illumination source(s) 42 and 42', and on, or in the vicinity of, plane BB, such that it receives incident light remitted from target 15 Other suitable arrangements may be possible. All or most of the light radiated from illumination source(s) 42 and 42' that may be internally reflected from the optical window surfaces may be received at points on focal curve D and may not be incident on imager 46.

Thus, in one embodiment, data obtained by imager 46 may be substantially free of backscatter and stray light In reality an illumination source cannot be confined to a focal curve D because the illumination source has a volume and surface area associated with it. For an illumination source 42 and 42' to be positioned on and/or significantly confined to the focal curve D, an assumption need be made that the illumination source 42 and 42' may be considered a point source, with no significant volume as compared to the volume of the ellipsoid dome 54. For an in-vivo device where dimensions may be relatively small, the volume of the illumination sources 42 and 42' may have significance as compared to the volume of the dome 54 and therefore such an assumption may lead to errors and part of the light from the illumination source reflected off of dome 54 may be incident on imager 46.

Figure 4:
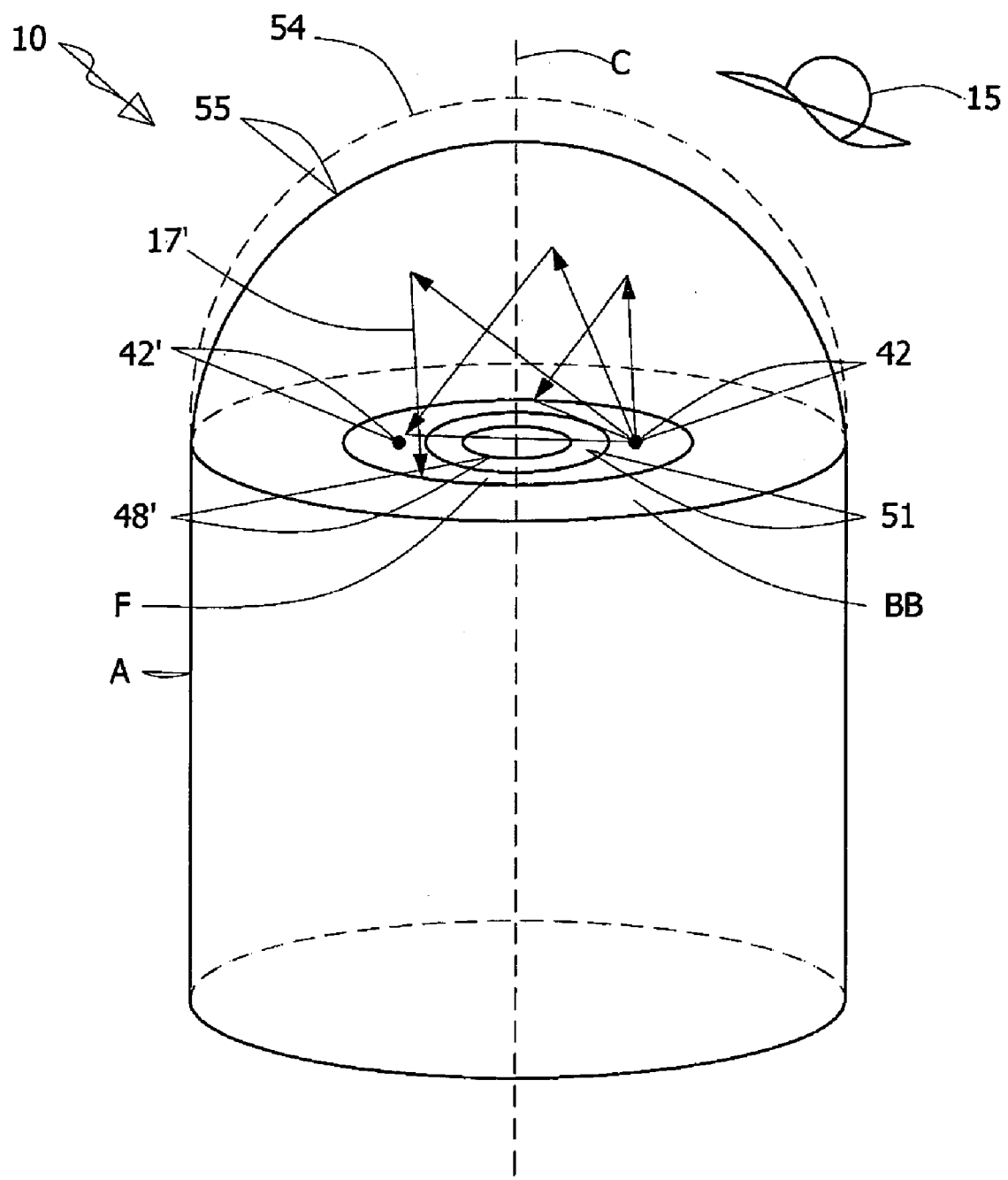
FIG. 4 is a schematic illustration of an optical system according to another embodiment of the present invention.

Reference is now made to FIG. 4 showing a cross section of an optical system having an optical window with a shape of a deformed ellipsoid, e.g. a slightly deformed ellipsoid. According to some embodiments of the present invention, the optical window 55, for example, the inner surface of the optical window 55 may have a shape of a slightly deformed ellipsoid and/or flattened ellipsoid. For example, window 55 may be slightly flattened as compared to an ideal ellipsoid 54 The deformation may have the effect of providing or defining a focal ring and/or isolated area F, e.g. a "backscatter ring" as opposed to a focal curve D (FIG. 3) where light rays originating from one point or position on the isolated area F and reflected off of surface 55 (e.g. inner or outer surface) may be incident on another position and/or point in the isolated area F and not incident on a central area 51 that may include an opening toward an image sensor, for example aperture 48'. The isolated area F may be positioned on a defined plane, for example, plane BB. Aperture 48' or another inlet to an imager 46 (FIG. 2) may be on the same plane as isolated area F As such backscatter toward the imager 46 (FIG. 2) may be avoided or substantially avoided for illumination source(s) that may be positioned within the area defined by isolated area F. Other shapes, for example, empirical shapes that may define an isolated area as may be described herein may be used According to one embodiment of the present invention, the optical dome 55 may have a shape that may define a backscatter area and/or an isolated area F, e.g. a confined area where backscatter may be incident, wherein illumination element 42 is positioned and a central area, e.g. 48', wherein a receiving element is positioned such that light from an illumination element originating from within the focal area when reflected off the optical dome may not be incident on said central area. According to one embodiment, the optical dome may have a shape of a section of a flattened/deformed ellipsoid. According to some embodiment of the present invention, images may be obtained with, for example, reduced or no backscatter, or stray light.

Figure 5:
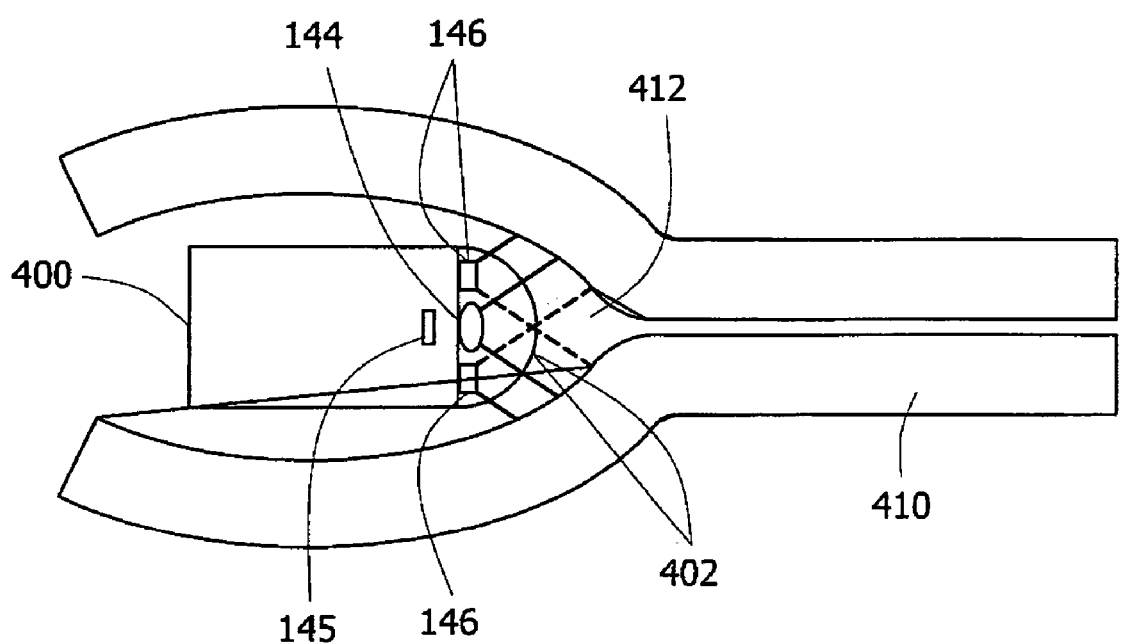
FIG. 5 is a schematic illustration of an in vivo imaging device within a body lumen according to an embodiment of the present invention.

Reference is now made to FIG. 5, which presents a schematic illustration of an in-vivo imaging device which may be used to view lumens such as the gastrointestinal tract, according to an embodiment of the present invention. Imaging device 400, e.g. an endoscope and/or autonomous imaging device may image lumens in an unmodified environment, but modification may be used as well. Imaging device 400 may be capable of being inserted and moved and/or self transported through for example the intestine 410; other lumens may be imaged. The dome or convex shaped tip 402 of imaging device 400 may include an optical window through which the intestine may be illuminated and viewed and/or imaged. Tip 402 or a portion thereof, such as a window, may be substantially transparent, and may present a forward projecting convex portion. Tip 402 may be similar to optical window 54 or optical window 55, described herein; however, other suitable tips, optical windows, or domes may be used One or more illumination sources 146, an imager 145 and a lens 144 may be positioned behind tip 402.

In some embodiments the spatial resolution of the viewing may be improved when using an embodiment of the present invention. One cause, in some embodiments, may be that insufflation that may be used in known endoscope procedures, may causes the intestine to be relatively cylindrically shaped. In a non-insufflated lumen and when using a device 400 according to some embodiments described herein, collapsed walls of the intestine may form a half-sphere around end 402 (which may include the optical dome) of the device 400. Typically, the optical path to the half sphere shaped lumen formed by the collapsed intestine walls may be a shorter optical path as compared to the optical path for imaging insufflated intestine walls. The collapsed, uninsufflated intestine walls 410 may be in close proximity to the imaging device 400 and present a field of view 412 illuminated by illumination sources 146 that may be imaged by imaging device 400. Other configurations for illumination fields or view fields may be used. Other numbers of illumination devices may be used.

Figure 6A:
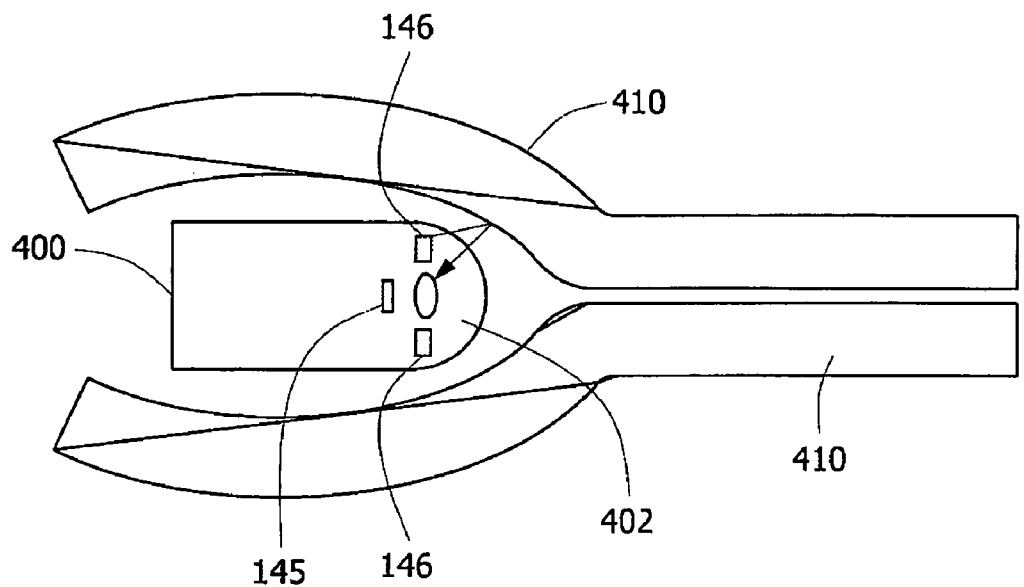
FIG. 6A is a depiction of an embodiment of the invention as compared to a prior art system.
Figure 6B:
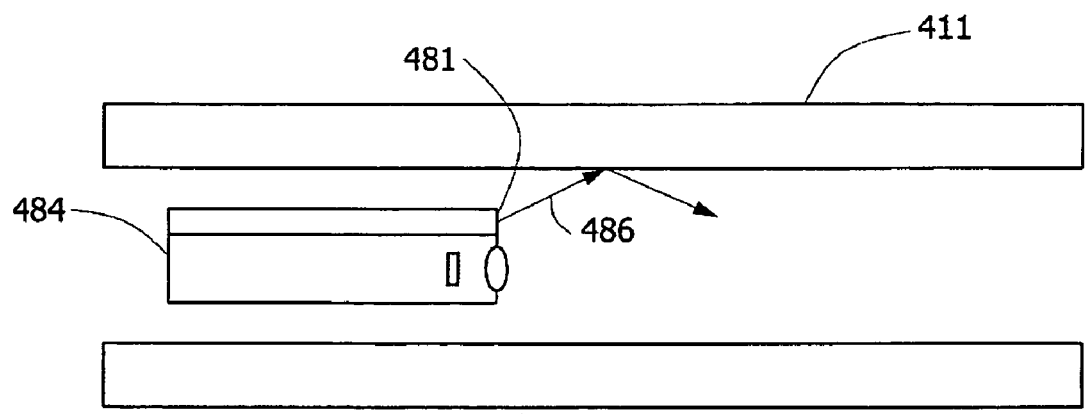
FIG. 6B is a depiction of prior art system compared to an embodiment of the present invention.

FIG. 6A is a depiction of an embodiment of the invention as compared, for example, to a prior art system shown in FIG. 6B. Referring to FIG. 6A, imaging device 400 may be a capsule, an endoscope or a portion of an endoscope, or another device, and may be structured and operated according to embodiments described herein. Lumen wall 410 may substantially wrapped device 400 so that most of the light originating from illumination sources 146 may be reflected from the lumen wall 410 back toward device 400 for imaging. The illumination efficiency of imaging device 400 may be higher than that of prior art imaging device 484, for example that may require insufflation due to, for example, the configuration of the end 481 of device 484. Insufflation may have the effect of moving the lumen wall 411 away from the end of device 484 and thus much of the light originating from device 484, e g light ray 486, may not be reflected back into device 484 for imaging.

According to some embodiments of the present invention, the proximity of the tip 402 of device 400 (FIG. 6A) to body lumen wall 410 may enable device 400 to image and/or discern through imaging formations such as arterioles, venulas, lymphatic ducts and others, which may be located submucosively and which may be viewed through a thinner layer of mucosa. This may not be possible when imaging with device 484 due to the longer distance between the tip 481, for example the tip of the illumination section, and the body lumen wall 486 and/or due to the longer optical path. Other benefits are possible, and other configurations of a device 400 according to embodiments of the invention may be possible.

Figure 7:
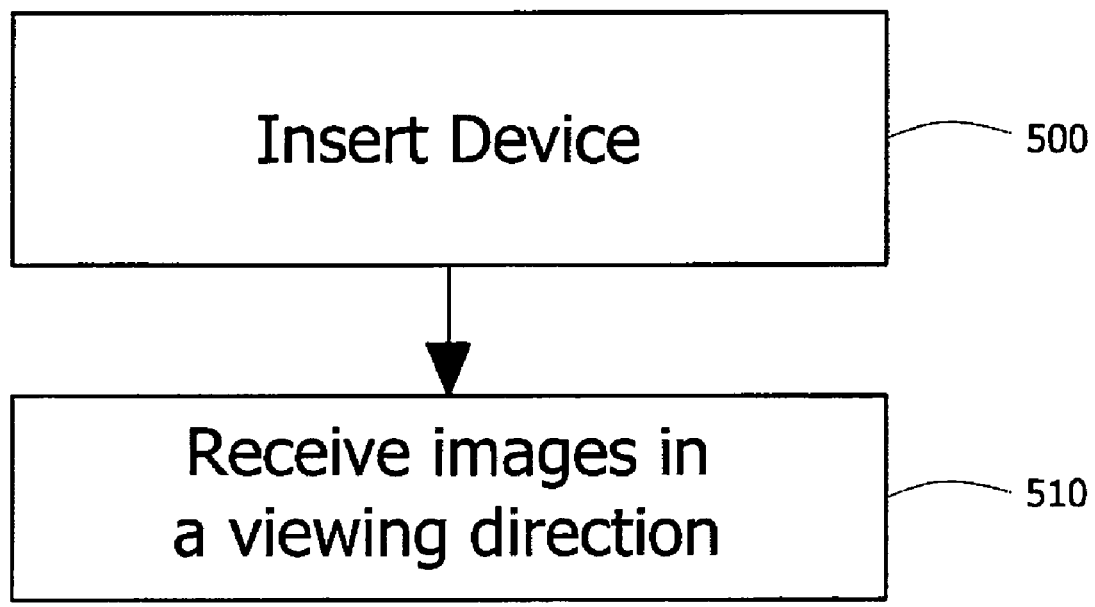
FIG. 7 is a flowchart depicting a method according to an embodiment of the present invention.

FIG. 7 is a flowchart depicting a method according to an embodiment of the present invention. Referring to FIG. 7, in step 500, a device may be inserted into a body lumen (e.g., by swallowing, inserting by aid of an endoscope, etc.). In step 510, images in the viewing direction may be captured by an imager within the device. The device may be a device similar to those depicted in embodiments herein; however, other suitable devices may be used. For example images may be taken through a substantially convex end. Other operations or series of operations may be used.

Figure 8A:
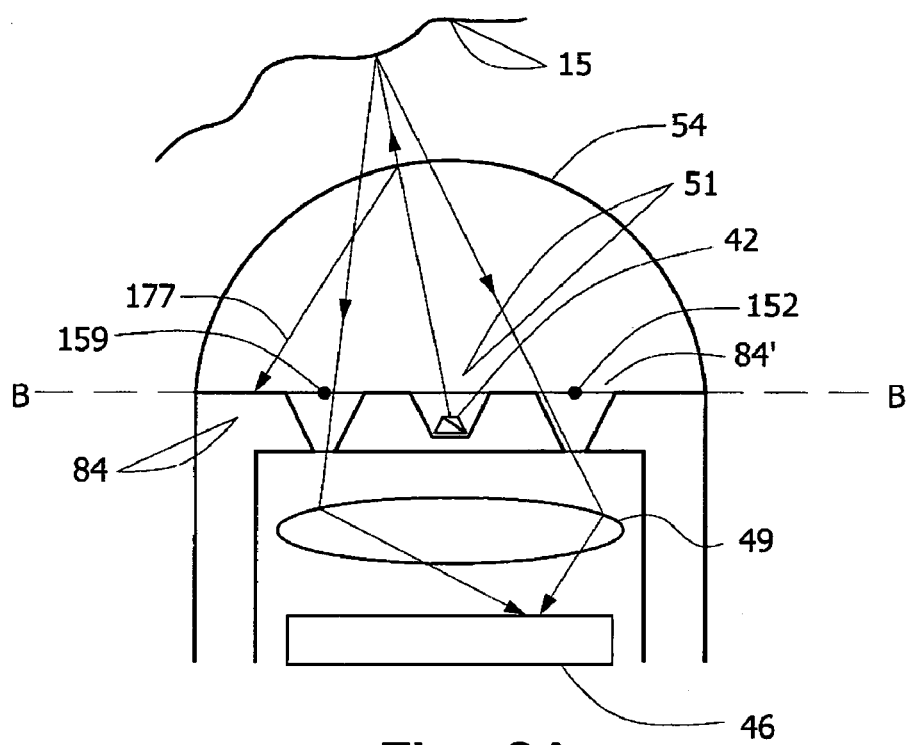
FIG. 8A is a schematic illustration of an optical system with an ellipsoidal optical window according to yet another embodiment of the present invention.
Figure 8B:
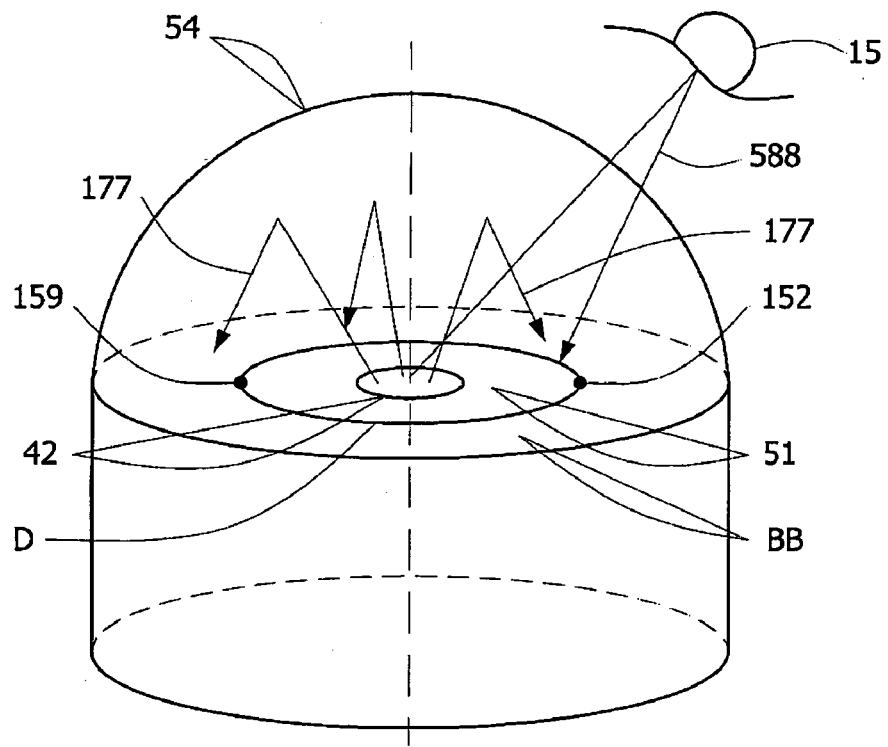
FIG. 8B is a schematic illustration of an optical system with a focal curve defined by the geometry of a viewing dome according to yet another embodiment of the present invention.

Reference is now made to FIG. 8A and FIG. 8B which is a schematic illustration of an optical system and a focal curve according to yet another embodiment of the present invention. In one embodiment of the present invention, one or more illumination sources 42 may be positioned in the central area 51 surrounded by a focal curve D, e.g. with focal points 152 and 159 defined by the ellipsoidal, or substantially ellipsoidal optical window 54 as may be described herein, while the inlet to the imager 46, for example imager 46, lens 49 or a ring shaped aperture 84' may be positioned and or confined to the defined focal curve D (FIG. 3). A ring of focal points including focal points 159 and 152 may form a circle, ring or other shape lying in a focal plane. Due to the defined shape of the ellipsoidal optical window 54, only light rays originating from a focal point, e.g. focal point 152 on the focal curve D may be reflected onto another focal point, e.g. focal point 159 on the focal curve D. Light rays originating from points other than the focal curve, e.g. light ray 177 originating from the central area 51 as may be described herein, may not be incident on any points on the focal curve defined by the ellipsoidal shape of the optical window 54. Baffle 84 may be used to prevent light from light source 42 from directly reaching imager 46 as well as to prevent backscatter that may occur in a the central area, e.g. a central area 51 not coinciding with the focal curve D, from reaching imager 46 According to one embodiment of the present invention, backscatter from light rays originating from light source 42 positioned in the central area may not be incident on imager 46 while light, e.g. light ray 588 reflected off a target 15 may be incident on focal curve D and reach imager 46 through aperture 84'. In other embodiment of the present invention lens 49 may be ring shaped or may have a bore corresponding to the central area In one embodiment of the present invention, light source 42 may be positioned in the bore and light rays reflected of target 15 may be directed to imager 46 by lens 49 substantially surrounding light source 42. According to one embodiment of the present invention, the optical window 54, common to both the imager 46 and light source 42, may have a geometry such that light rays reflected back from optical window 54 may not be incident to an inlet of imager 46 while light rays reflected off a target 15 may be incident to an inlet to imager 46. According to another embodiment of the present invention, a light sensitive area of imager 46 may be ring shaped.

Figure 9A:
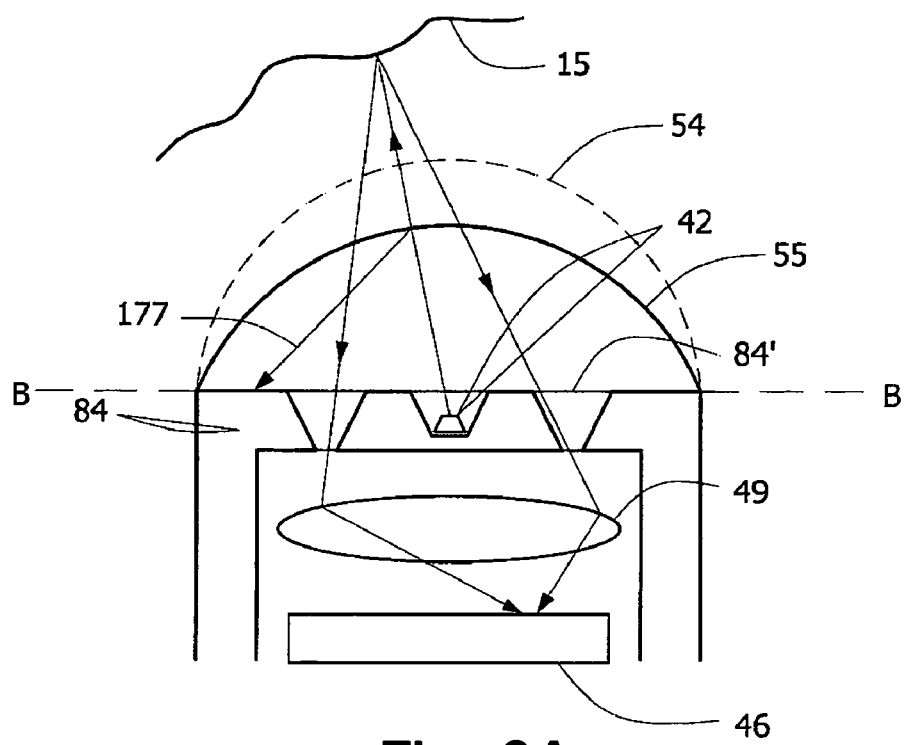
FIG. 9A is a schematic illustration of an optical system with a deformed ellipsoidal optical window according to yet another embodiment of the present invention.
Figure 9B:
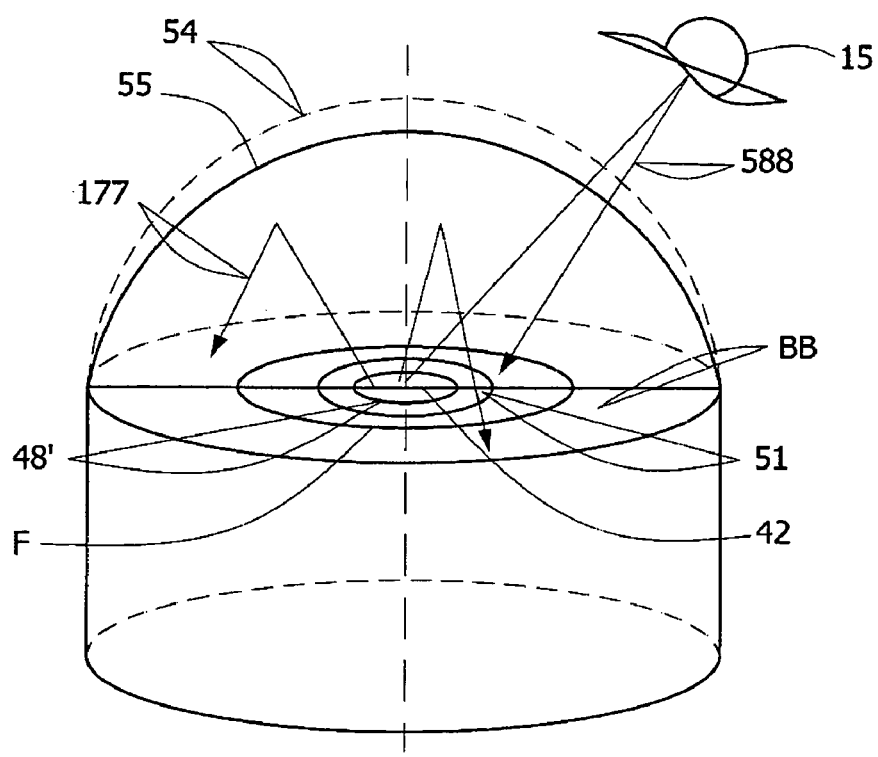
FIG. 9B is a schematic illustration of an optical system with a isolated area defined by the geometry of a viewing dome according to yet another embodiment of the present invention.

Reference is now made to FIGS. 9A and 9B which is a schematic illustration of an optical system with a slightly deformed ellipsoidal optical window, e.g. slightly flattened ellipsoid, according to yet another embodiment of the present invention. In one embodiment of the present invention, one or more illumination sources 42 may be positioned in a central area 51 as defined herein, while the inlet to the imager 46, for example ring shaped aperture 84', imager 46, or lens 49 may be positioned and or confined to the isolated area F defined by the geometry of the slightly deformed ellipsoid as may be described herein. Due to the defined shape of the deformed ellipsoidal optical window 55, backscatter due to to a point in the isolated area may only occur from an illumination source positioned on a point in that isolated area. Light rays originating from points other than points in the isolated area, for example from light 177 from light source 42 positioned in central area 51 and reflected off of dome 55 may not be incident anywhere in that isolated area F defined by the deformed ellipsoidal shape of the optical window 54. Baffle 84 may be used to prevent light from light source 42 from directly reaching imager 46 as well as to prevent backscatter that may occur in the central area. According to one embodiment of the present invention, backscatter from light rays originating from light source 42 positioned in the central area, may not be incident on imager 46. Light, e.g. light ray 588 reflected off a target 15 may be incident on image 46 via isolated area F.

It will be appreciated by persons skilled in the art that the present invention is not limited to what has been particularly shown and described hereinabove. Alternate embodiments are contemplated which fall within the scope of the invention. In addition, aspects of the various embodiments disclosed herein are combinable with the other embodiments disclosed herein.

The invention claimed is:

1. An autonomous in-vivo imaging device comprising:
a device body having a longitudinal axis, the device body comprising an optical dome;
an illumination source; and
an imager;
wherein said optical dome covers said illumination source and said imager;
wherein said illumination source is positioned along a curve that defines the foci of an ideal ellipsoid, wherein said ideal ellipsoid intersects the device body; and
wherein said optical dome has a shape of a convex surface flattened from said ideal ellipsoid in a direction along the longitudinal axis, wherein said shape of said convex surface is flattened so that light emitted from said illumination source that reflects off of said flattened optical dome is reflected onto a ring-shaped region of a plane of said illumination source and not on said imager.

2. The device of claim 1, wherein the device is a capsule.

3. The device of claim 1 comprising a baffle wherein the baffle substantially encompasses said imager and wherein the baffle comprises an aperture.

4. The device according to claim 3 wherein said aperture defines an opening positioned on the longitudinal axis.

5. The device of claim 3, wherein said shape of said optical dome causes backscattering of light emitted from the illumination source away from said aperture.

6. The device of claim 3, comprising a plurality of illumination sources positioned along said focal curve of said ideal ellipsoid, wherein said optical dome causes backscattering light emitted from said plurality of illumination sources to a ring about the focal curve of said ideal ellipsoid and outside said aperture.

7. The device of claim 6, wherein said aperture and said plurality of illumination sources are positioned on the same plane.

8. An autonomous in-vivo imaging device comprising:
an optical dome;
a plurality of illumination sources positioned along a curve that defines the foci of an ideal ellipsoid, wherein the ideal ellipsoid intersects the body of the imaging device; and
an imager;
the imager and the illumination sources being behind the optical dome, the imager accepting images via the optical dome through an aperture positioned on the longitudinal axis of the device;
wherein the optical dome has a shape of a convex surface flattened from said ideal ellipsoid in a direction along the longitudinal axis, wherein said shape of said convex surface is flattened causing the backscattering of light emitted from said plurality of illumination sources onto a ring-shaped region of a plane about the focal curve of the ideal ellipsoid and outside the aperture.

9. The device according to claim 8 wherein the device is an autonomous capsule.

10. The device according to claim 8 wherein the illumination sources illuminate through the optical dome.

11. The device according to claim 8 wherein the ring and the aperture lie in a common plane.

12. The device according to claim 8 comprising a baffle that forms the aperture for receiving light remitted from a target.

13. The device according to claim 8 wherein the optical dome includes an inner surface and wherein light of said illumination source is reflected from said inner surface and is incident on said ring.

14. The device according to claim 8 wherein the optical dome includes an external surface and wherein light of said illumination sources is reflected from said external surface and is incident on said ring.

15. An autonomous in-vivo imaging device comprising:
an imager;
an illumination source; and
an optical dome, covering the imager and illumination source, wherein said illumination source is positioned along a curve that defines the foci of an ideal ellipsoid, wherein said ideal ellipsoid intersects the body of said imaging device, wherein said optical dome has a shape of a convex surface flattened from said ideal ellipsoid in a direction along a longitudinal axis of said imaging device, wherein said shape of said convex surface is flattened so that light emitted from said illumination source that reflects off of said flattened optical dome is refected onto a ring-shaped region of a plane of said illumination source and not on said imager.

16. The device according to claim 15 wherein the device is capsule.

17. The device of claim 15, wherein said imaging device comprises an aperture through which said imager accepts images, wherein said aperture is positioned on the longitudinal axis.

18. The device of claim 17, wherein said shape of said optical dome causes backscattering of light emitted from said illumination source away from said aperture.

19. The device of claim 17, comprising a plurality of illumination sources positioned along said focal curve of said ideal ellipsoid, wherein said optical dome causes backscattering of light emitted from said plurality of illumination sources to a ring about the focal curve of said ideal ellipsoid and outside said aperture.

20. The device of claim 19, wherein said aperture and said plurality of illumination sources are positioned on the same plane.

* * * * *